United States Patent
Ikhlef et al.

(10) Patent No.: US 11,602,317 B2
(45) Date of Patent: Mar. 14, 2023

(54) APPARATUS AND METHOD FOR MODULE ALIGNMENT IN CT DETECTOR

(71) Applicant: Minfound Medical Systems Co. Ltd., Hangzhou (CN)

(72) Inventors: Abdelaziz Ikhlef, Hudson, OH (US); Mark McElroy, Akron, OH (US)

(73) Assignee: Minfound Medical Systems Co., Ltd., Hangzhou (CN)

( * ) Notice: Subject to any disclaimer, the term of this patent is extended or adjusted under 35 U.S.C. 154(b) by 141 days.

(21) Appl. No.: 17/237,581

(22) Filed: Apr. 22, 2021

(65) Prior Publication Data
US 2022/0338823 A1    Oct. 27, 2022

(51) Int. Cl.
*G01T 7/00* (2006.01)
*A61B 6/00* (2006.01)
*A61B 6/03* (2006.01)

(52) U.S. Cl.
CPC ............ *A61B 6/4266* (2013.01); *A61B 6/035* (2013.01); *A61B 6/4233* (2013.01); *A61B 6/4291* (2013.01); *A61B 6/4435* (2013.01)

(58) Field of Classification Search
CPC ..... A61B 6/4266; A61B 6/035; A61B 6/4291; A61B 6/4435; A61B 6/4233; A61B 6/032; A61B 6/037; A61B 6/44; A61B 6/4429; A61B 6/4452; G01T 1/2018
See application file for complete search history.

(56) References Cited

U.S. PATENT DOCUMENTS

| | | | |
|---|---|---|---|
| 8,824,635 B2 | 9/2014 | Tkaczyk et al. | |
| 9,168,008 B2 | 10/2015 | Ikhlef et al. | |
| 9,519,069 B2 | 12/2016 | Lacey et al. | |
| 9,952,338 B2* | 4/2018 | Pohan | G01N 23/046 |
| 10,473,796 B2 | 11/2019 | Ikhlef et al. | |
| 10,492,746 B2 | 12/2019 | Ikhlef | |
| 2012/0166128 A1 | 6/2012 | Ikhlef et al. | |
| 2020/0000422 A1 | 1/2020 | Yu et al. | |

FOREIGN PATENT DOCUMENTS

EP    2438864 A1    4/2012

* cited by examiner

*Primary Examiner* — Don K Wong
(74) *Attorney, Agent, or Firm* — Fishman Stewart PLLC (57) ABSTRACT

A detector sub-assembly for a CT system includes a detector module that includes a mount block having a top planar surface, a Y-axis planar surface that is parallel with the top planar surface, an X-axis planar surface that is orthogonal to the first Y-axis planar surface, and an aperture passing through the X-axis planar surface. The module includes a substrate having a pixelated photodiode positioned thereon, and a two-dimensional anti-scatter grid (ASG) positioned on the pixelated photodiode. The detector sub-assembly includes a support structure including a Y-axis mount surface and an X-axis mount surface, and a second aperture passing through the X-axis mount surface, a mounting screw having an outer diameter that is smaller than an inner diameter of the aperture and passing through the aperture and into the second aperture when the Y-axis planar surface is on the Y-axis mount surface.

20 Claims, 12 Drawing Sheets

APPARATUS AND METHOD FOR MODULE ALIGNMENT IN CT DETECTOR

TECHNICAL FIELD

This disclosure relates generally to diagnostic imaging and, more particularly, to an apparatus and method of aligning a module in a computed tomography (CT) detector.

BACKGROUND

Typically, in computed tomography (CT) imaging systems, a rotatable gantry includes an x-ray tube, detector, data acquisition system (DAS), and other components that rotate about a patient table that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into visible light photons within the scintillator, and then to electrical signals within the photodiode. The electrical signals are digitized and then received and processed within the DAS. The processed signals are transmitted via a slipring (from the rotational side to the stationary side) to a computer for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Third generation multi-slices CT scanners typically include detectors having scintillator/photodiodes arrays. These detectors are positioned in an arc where the focal spot is the center of the corresponding circle. These detectors generally have scintillation crystal/photodiode arrays, where the scintillation crystal absorbs x-rays and converts the absorbed energy into visible light. A photodiode is used to convert the light to an electric current. The reading is typically linear to the total energy absorbed in the scintillator.

Typically, CT systems obtain raw data and then reconstruct images using various known pre-processing and post-processing steps to generate a final reconstructed image. That is, CT systems may be calibrated to account for x-ray source spectral properties, detector response, and other features, to include temperature. Raw x-ray data are pre-processed using known steps that include offset correction, reference normalization, and air calibration steps, as examples.

In recent years, the development of volumetric or cone-beam CT technology has led to an increase in the number of slices used in CT detectors for computed tomography systems. The detector technology used in large coverage CT enables greater coverage in patient scanning by increasing the area exposed, by using back-illuminated photodiodes. A typical detector includes an array of 16, 32, or 64 slices. However, the need for cardiac imaging has become of greater interest to enable imaging of the heart within one rotation of the detector, substantially increasing the width of the detector in the Z-axis (e.g., along the patient length), leading to a detector having 256 or more slices. Because it is impractical to build very large modules in monolithic structure to cover this number of slices and this width in the Z-axis, due to manufacturing cost and reliability concerns, smaller modules (mini-modules) are built along the Z-axis and placed along the Z-axis to build the overall length of 256 or more slices.

However, alignment of such modules presents various challenges due to the increased length of the detectors, along the Z-axis. Tolerances can stack along the Z-axis and it can be difficult to control the tolerance stack up as the modules are assembled onto a detector structure. In addition, not only may there be expensive and time-consuming procedures developed for assembly when in a manufacturing facility, it is difficult to apply such techniques to a detector that is installed (such as in a hospital suite). From time to time it is necessary to replace a module, such as if there is a failure that develops in an installed unit, so it may be impractical and very costly to remove an entire detector assembly from an installed CT system to have a failed module replaced.

Thus, there is a need to improve assembly of modules in a CT detector.

BRIEF DESCRIPTION

The disclosure is directed toward an apparatus and method of positioning detector modules in a support structure or detector sub-assembly for a CT system.

According to one aspect, a detector sub-assembly for a CT system includes a detector module that includes a mount block having a top planar surface, a Y-axis planar surface that is parallel with the top planar surface, an X-axis planar surface that is orthogonal to the first Y-axis planar surface, and an aperture passing through the X-axis planar surface. The module includes a substrate having a pixelated photodiode positioned thereon, and a two-dimensional anti-scatter grid (ASG) positioned on the pixelated photodiode. The detector sub-assembly includes a support structure including a Y-axis mount surface and an X-axis mount surface, and a second aperture passing through the X-axis mount surface, a mounting screw having an outer diameter that is smaller than an inner diameter of the aperture and passing through the aperture and into the second aperture when the Y-axis planar surface is on the Y-axis mount surface.

According to another aspect, a method of assembling a detector assembly for a CT system thereby includes providing a support structure that includes a first Y-axis mount surface and a second Y-axis mount surface, positioning a first detector module on the first Y-axis mount surface, the first detector module including a first mount block having a first top planar surface, a first Y-axis planar surface that is parallel with the first top planar surface, a first X-axis planar surface that is orthogonal to the first Y-axis planar surface, and a first aperture passing through the first X-axis planar surface, a first substrate having a first pixelated photodiode positioned thereon, and a first two-dimensional anti-scatter grid (ASG) positioned on the first pixelated photodiode. The method further includes attaching the first detector module to the first Y-axis mount surface of the support structure by passing a first mounting screw through the first aperture and into a second aperture that is in the support structure, the first mounting screw having an outer diameter that is smaller than an inner diameter of the first aperture.

Also according to an aspect, a CT system includes a rotatable gantry having an opening for receiving an object to be scanned, an x-ray tube having a focal spot from which x-rays emit, and a detector sub-assembly. The detector sub-assembly includes a first detector module that includes a first mount block having a first top planar surface, a first Y-axis planar surface that is parallel with the first top planar surface, a first X-axis planar surface that is orthogonal to the first Y-axis planar surface, and a first aperture passing through the first X-axis planar surface, a first substrate having a first pixelated photodiode positioned thereon, and a first two-dimensional anti-scatter grid (ASG) positioned on the first pixelated photodiode. A support structure includes a first Y-axis mount surface and a first X-axis mount surface, and a second aperture passing through the first X-axis mount surface, and a first mounting screw having an outer diameter that is smaller than an inner diameter of the of the first aperture and passing through the first aperture and into the second aperture when the first Y-axis planar surface is on the first Y-axis mount surface.

Various other features and advantages will be made apparent from the following detailed description and the drawings.

DETAILED DESCRIPTION

The operating environment of disclosed embodiments is described with respect to a 128/256/512-slice computed tomography (CT) system. Embodiments are described with respect to a "third generation" CT scanner, however it is contemplated that the disclosed embodiments are applicable to other imaging systems as well, and for CT systems having more or less than the illustrated sixteen-slice system.

Figure 1:
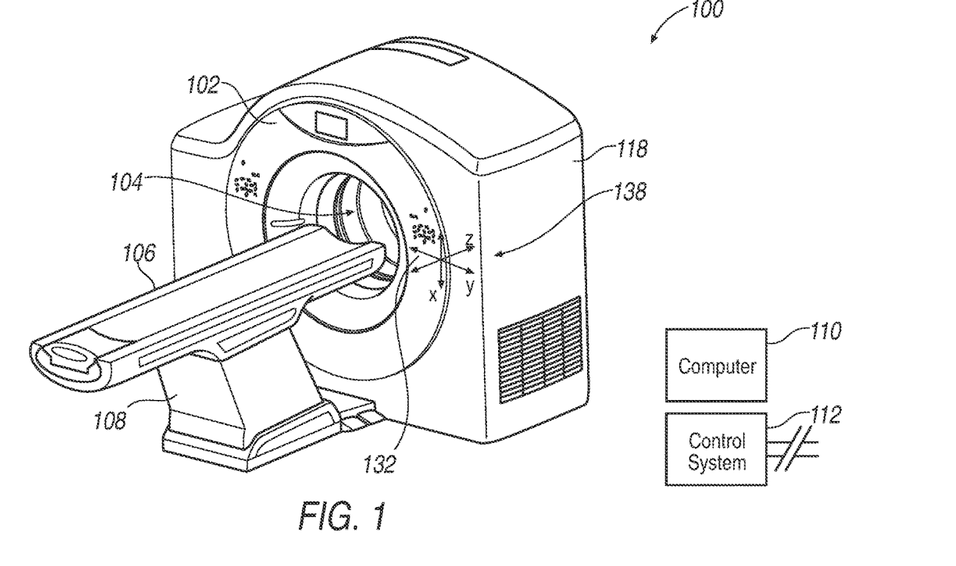
FIG. 1 is a perspective view of a CT imaging system.
Figure 2:
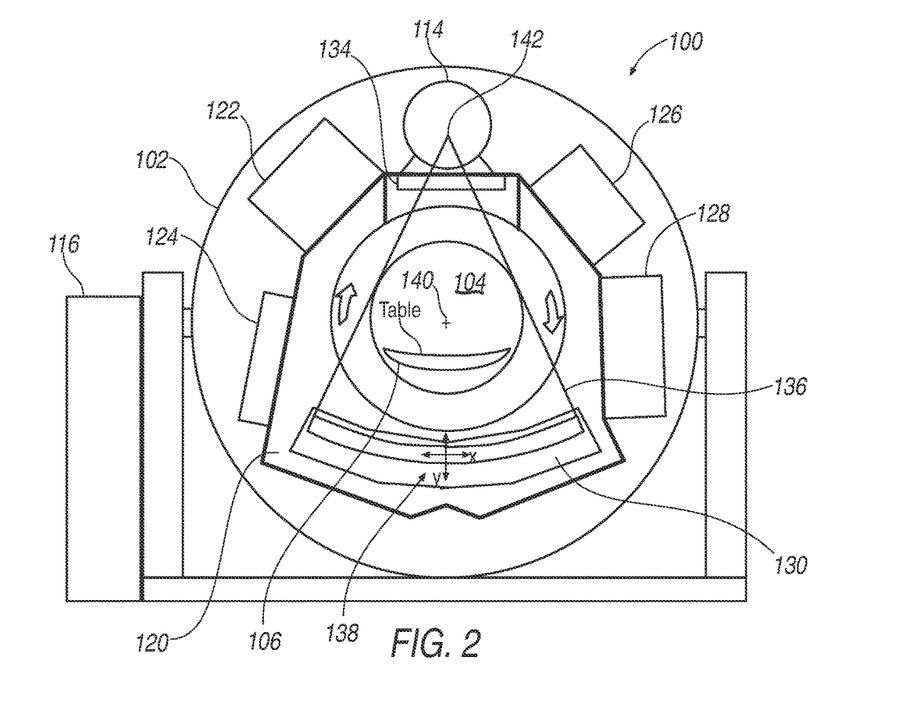
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed or more, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals that are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and a gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
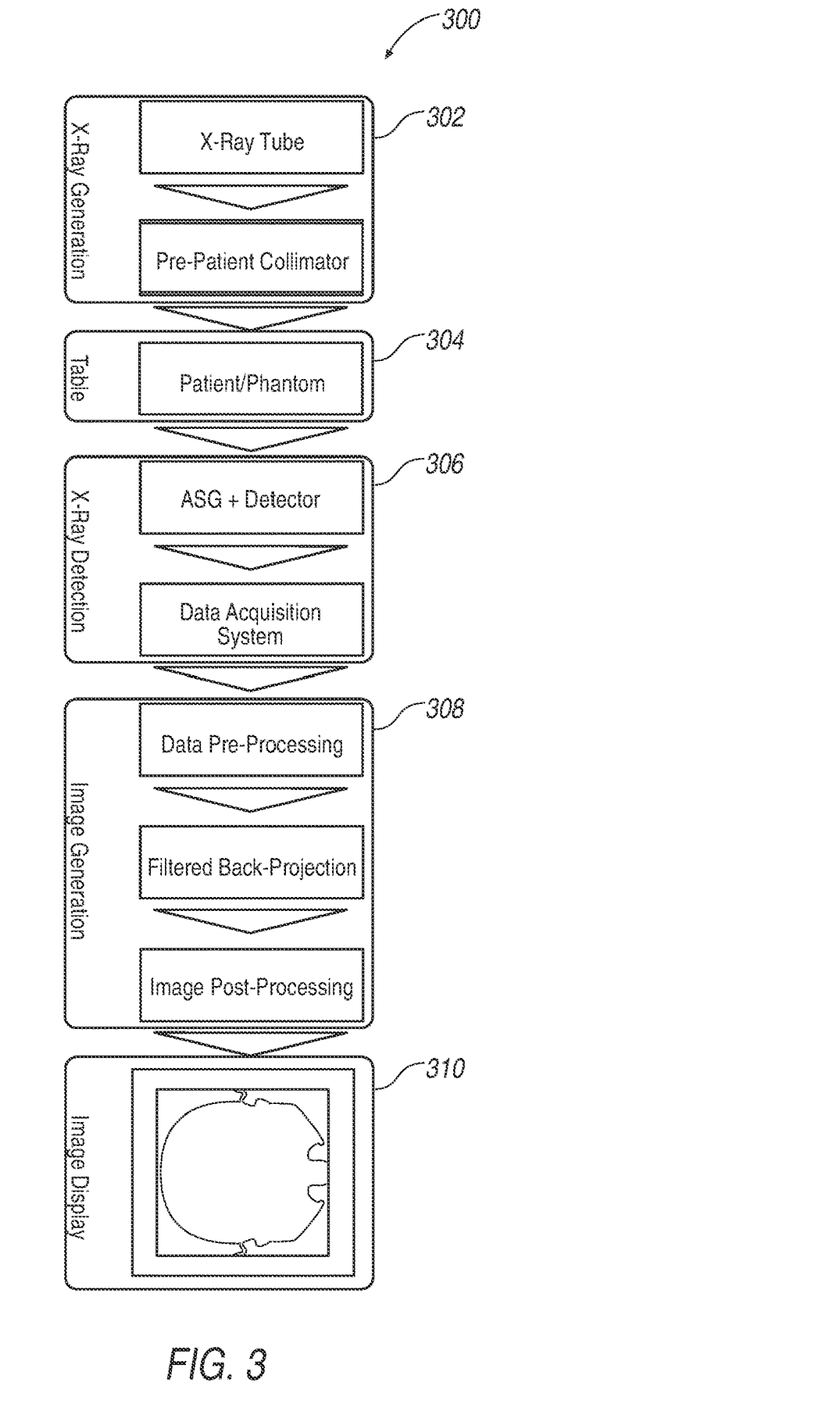
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which time table 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered back projection (FBP). Image post-processing also occurs, after which the images may be displayed 310, or otherwise made available for display elsewhere (such as in a remote computing device).

Figure 4:
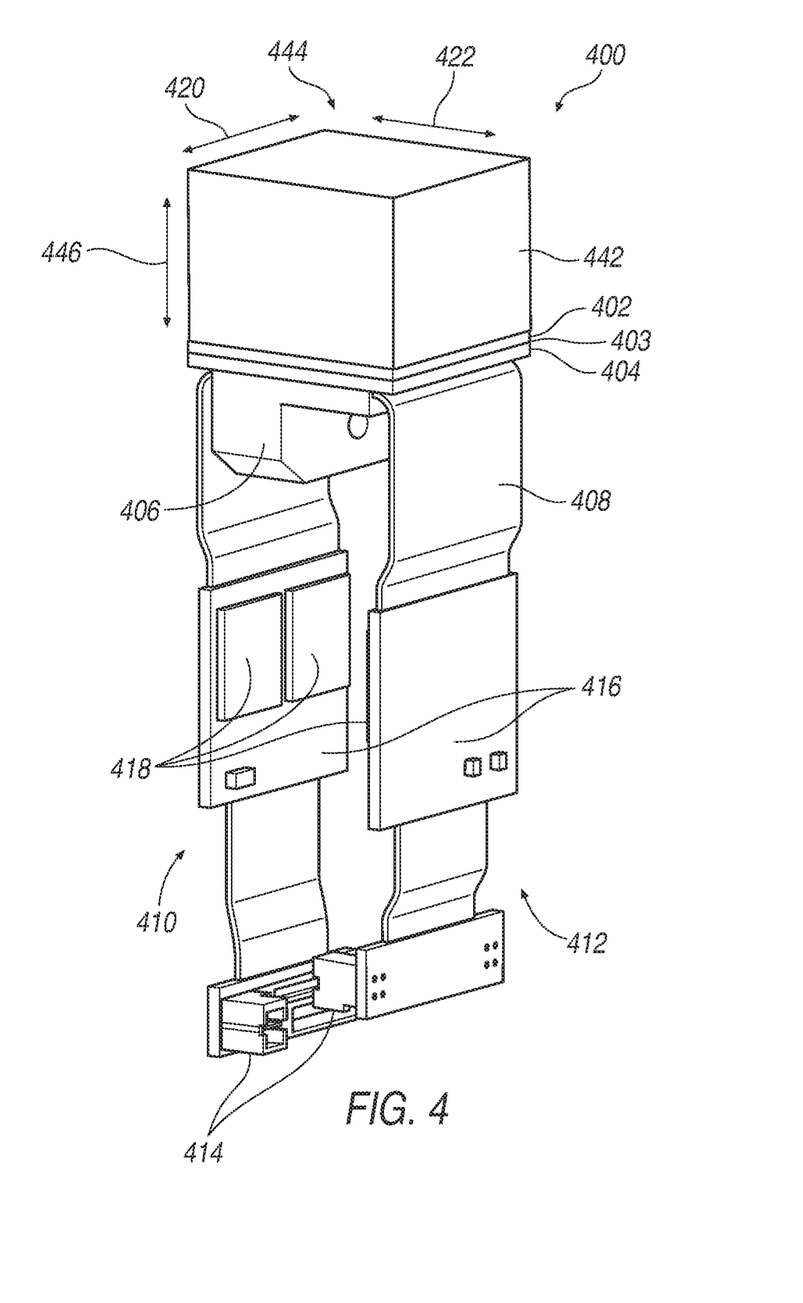
FIG. 4 illustrates a module or mini-module having a collimator attached thereto.

FIG. 4 illustrates a mini-module 400 having been assembled according to the disclosure. Mini-module 400 includes a grid of pixelated scintillators or scintillating array 402 positioned on a substrate 404, having a photodiode 403 therebetween. An alignment block or support structure 406 mechanically supports mini-module 400. Positioned between support structure 406 and substrate 404 is a flex circuit 408, which wraps within mini-module 400 and includes a first end 410 and a second end 412. Each end 410, 412 includes electrical connectors 414, a circuit board or electronics package 416, ASIC or processors 418, and other associated electronic components (not shown). Mini-module 400, when placed on a gantry of a CT system, such as system 100 above, in one example, has an orientation of a Z or slice direction 420 and an X or channel direction 422.

An anti-scatter grid 442 having a plurality of plates 444 is positioned on an upper surface of scintillating array 402. In the example shown, anti-scatter grid 442 is a monolithic device having plates that extend in X or channel direction 422, or may have plates that extend in both X or channel direction 422, as we as Z or slice direction 420. Anti-scatter grid 442 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 442 is a two-dimensional (2D) collimator with plates 444 spaced from one another having a spacing that corresponds with a spacing of pixels.

Plates 444 may thereby be fabricated in anti-scatter grid 442 to be slightly non-parallel to one another so that each may be directed and approximately aimed toward a focal spot of a CT system. For instance, referring to FIG. 2, mini-modules 400 may be positioned accordingly within CT detector assembly 130 and on gantry 102, having each plate 444 extending along a length and in a direction 446 such that, when CT detector 130 is positioned in CT system 100, the length of plates 444 extend 446 approximately toward focal spot 142 of CT system 100.

Figure 5:
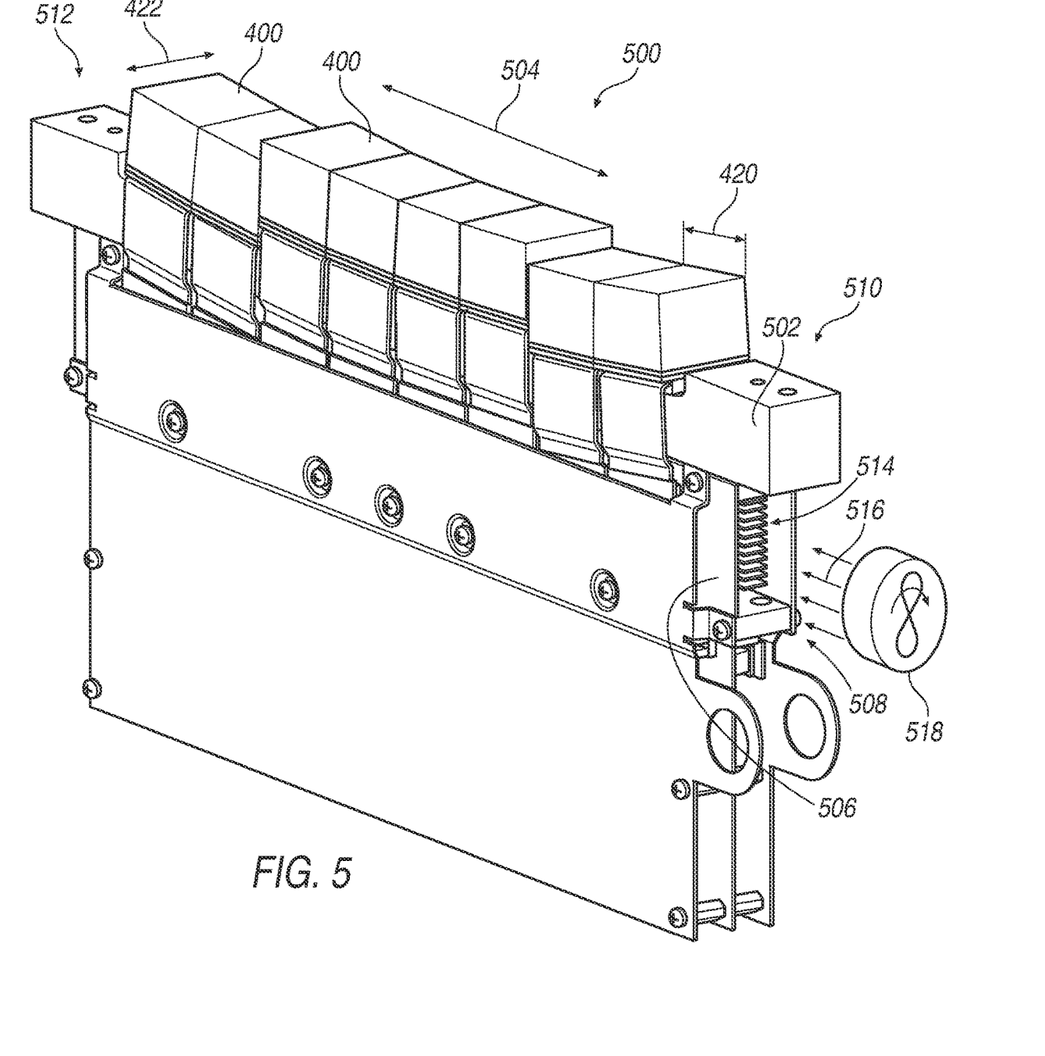
FIG. 5 a detector sub-assembly having a plurality of modules.

Referring now to FIG. 5, a detector sub-assembly (module) 500 shows a plurality of mini-modules 400, being positioned on an alignment block 502. As shown, each mini-module 400 includes Z or slice direction 420, which combine to provide a composite coverage in a system Z direction 504, which corresponds with triad 138 in FIGS. 1 and 2. Correspondingly, each mini-module 400 includes X or channel direction 422, and modules 400 are thereby combined or stacked side-by-side to form a plurality of detectors, corresponding with triad 138 of FIGS. 1 and 2, forming detector assembly 130. Thus, according to the disclosure, each mini-module 400 is fabricated in the fashion described herein. As such, global system tolerances do not accumulate, such as if all plates 444 were placed with respect to alignment block 502, for example. In addition, each mini-module 400 may be classified and placed within the detector according to the measured quality of the modules.

Referring still to FIG. 5, a detector assembly or sub-assembly 500 shows a plurality of mini-modules 400, being positioned on an alignment block 502. As shown, each mini-module 400 includes Z or slice direction 420, which combine to provide a composite coverage in a system Z direction 504, which corresponds with triad 138 in FIGS. 1 and 2. Correspondingly, each mini-module 400 includes X or channel direction 422, and mini-modules 400 are thereby combined or stacked side-by-side to form a plurality of detectors, corresponding with triad 138 of FIGS. 1 and 2, forming detector assembly 130.

Thus, according to the disclosure, a detector assembly 500 for CT system 100 includes plurality of detector mini-modules 400, each detector module including a grid of pixelated scintillators 402, a reflector (as is commonly known), a photodiode 403 having pixelations that correspond with the pixelated scintillators 402, and an electronics package 416 for processing acquired X-ray data. A support structure 502, corresponding with support structure 406 above, extends along Z-direction 504 of CT system 100 and includes plurality of detector mini-modules 400 positioned thereon. A heat sink 506 extends along Z-direction 504 and includes support structure 502 mounted thereon. Heat sink 504 includes a passageway 508 passing therethrough and along Z-direction 504, such that cooling air may pass into passageway 508 at a first end 510 of heat sink 506 and exit passageway 508 at a second end 512 of heat sink 506 opposite first end 510. Heat sink 506 includes a plurality of fins or plates 514 positioned within passageway 508 and are thermally coupled to heat sink 506, each of plurality of plates 508 extending along Z-direction 504. As such, air or another cooling medium 516 is blown into passageway 508 via a fan, as an example, represented by element 518 in FIG. 5.

Figure 6:
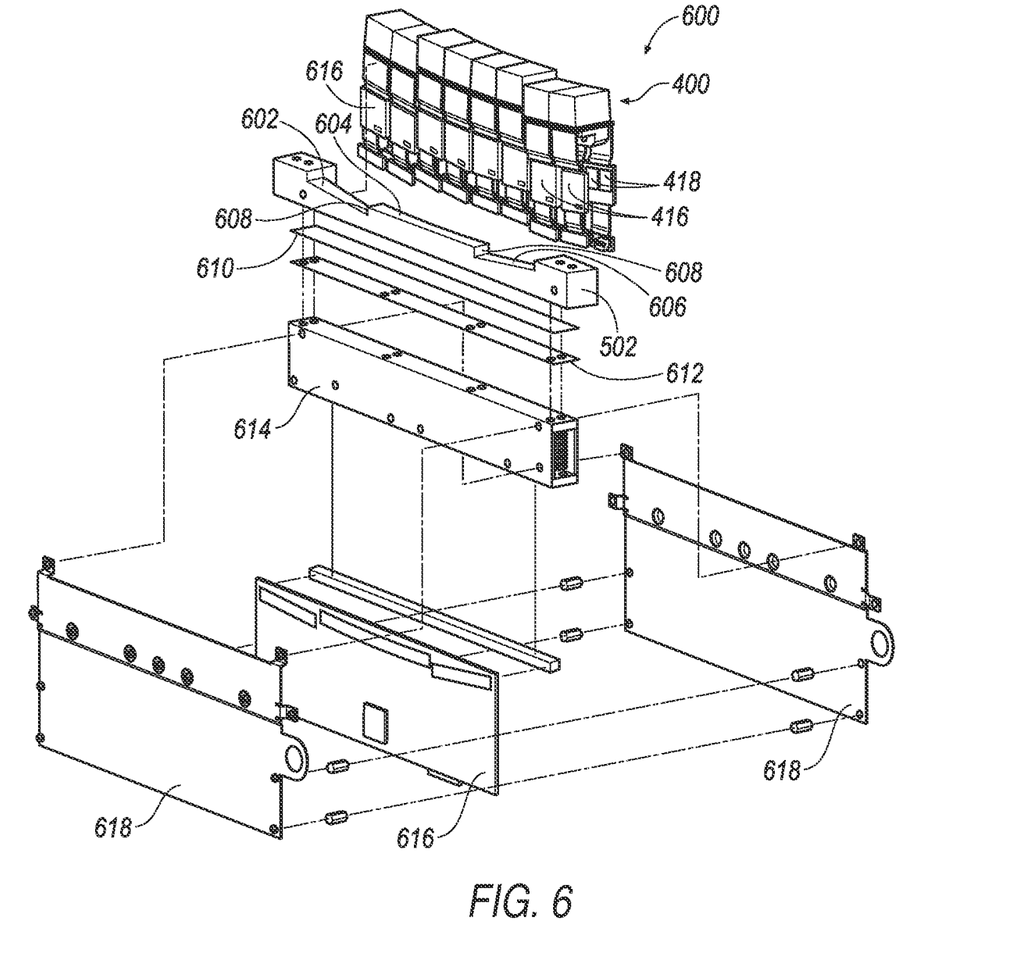
FIG. 6 illustrates an exploded and perspective view that includes the detector sub-assembly of FIG. 5.

Referring to FIG. 6, an exploded and perspective view 600 of detector assembly 500 is shown. Modules, or mini-modules 400 are shown proximate one another, and proximate support structure 502. Support structure 502 includes surfaces 602, 604, 606 which include steps 608. And, surfaces 602, 604, 606 may themselves include non-parallel surfaces such that each individual mini-module 400 may be directly aimed toward focal spot 142, regardless of which step it is positioned on.

Also, according to the disclosure detector assembly 500 includes a heater 610 and a thermal barrier 612. Detector assembly 500 includes a heat sink 614, a FPGA printed circuit board 616, and support plates 618. As known in the art, thermal control is an important aspect of detector design, and thus heater 610 uniformly heats support structure 502, thereby maintaining each of mini-modules 400 at uniform temperature during calibration and use. Thermal barrier 612 reduces the propensity for heat to flow from ASIC or processors 418 on each of circuit board or electronics package 416. Heat sink 614 is thermally coupled to each circuit board or electronics package 416, preventing heat from flowing to support structure 502 to negatively affect thermal calibration or performance of the detectors.

Figure 7:
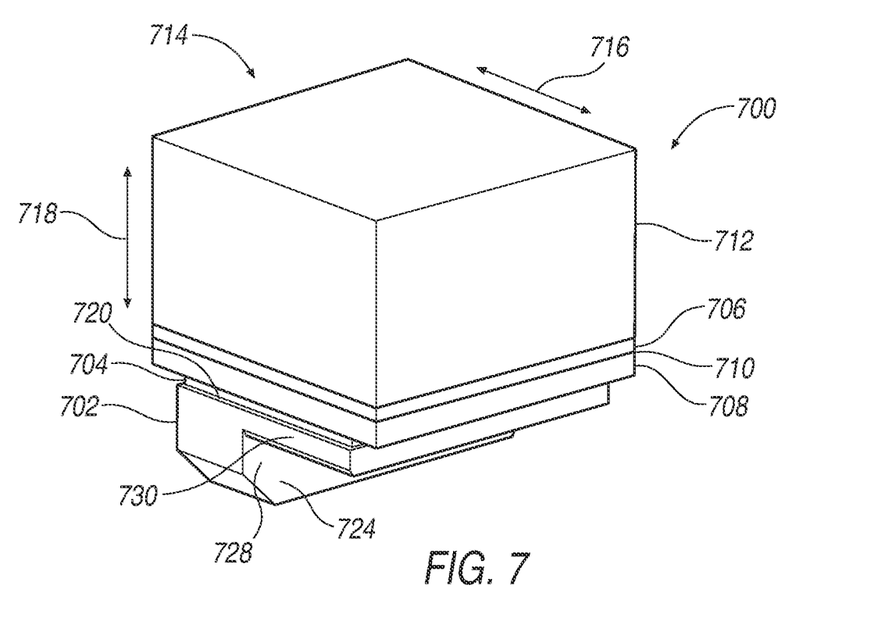
FIG. 7 illustrates a top perspective view of a sub-assembly corresponding with that of FIG. 4.
Figure 8:
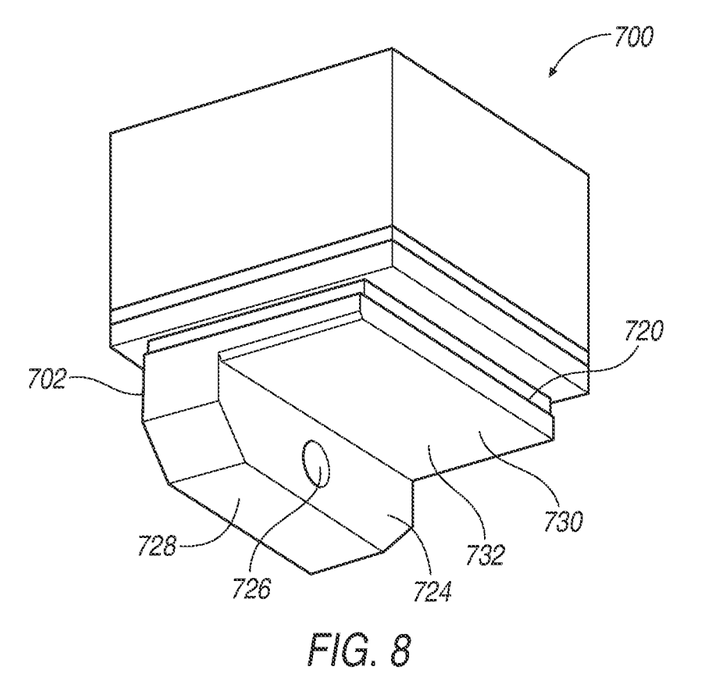
FIG. 8 illustrates a bottom perspective view of a sub-assembly corresponding with that of FIG. 4.

Referring to FIGS. 7 and 8, respective top and bottom perspective views of a sub-assembly 700 of FIG. 4 are illustrated. Sub-assembly 700 includes elements that correspond with FIGS. 4, 5, and 6, but have been renumbered for illustration and discussion purposes related to assembly of the various components as disclosed herein. Sub-assembly 700 includes and a mount block 702, and a flex circuit 704 positioned thereon. Flex circuit 704 is illustrated in a truncated fashion, for discussion purposes and for simplicity of illustration, but it is contemplated that flex circuit 704 corresponds with flex circuit 408 illustrated herein, such as in FIGS. 4, 5, and 6 (and having ends 410, 412, electrical connectors 414, circuit board or electronics package 416, ASIC or processors 418, and other associated electronic components (not shown)).

Sub-assembly 700 includes a grid of pixelated scintillators or scintillating array 706 positioned on a substrate 708, having a photodiode 710 therebetween. An anti-scatter grid (ASG) 712 having a plurality of plates 714 is positioned on an upper surface of scintillating array 706. In the example shown and as also disclosed in FIG. 4, anti-scatter grid 712 is a monolithic device having plates that extend in X or channel direction 716, as well as a Z-direction 824. Anti-scatter grid 712 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 712 is a two-dimensional (2D) collimator with plates 714 spaced from one another having a spacing that corresponds with a spacing of pixels.

Plates 714 may thereby be fabricated in anti-scatter grid 712 to be slightly non-parallel to one another so that each may be directed and approximately aimed toward a focal spot of a CT system. For instance, referring again to FIG. 2, sub-assemblies 700 may be positioned accordingly within CT detector assembly 130 and on gantry 102, having each plate 714 extending along a length and in a direction 718 such that, when CT detector 130 is positioned in CT system 100, the length of plates 714 extend 718 approximately toward focal spot 142 of CT system 100.

Mount block 702 includes a top planar surface 720, a Y-axis planar surface 722 that is parallel with top planar surface 720, an X-axis planar surface 724 that is orthogonal to Y-axis planar surface 722, and an aperture 726 passing through X-axis planar surface 724.

Figure 9:
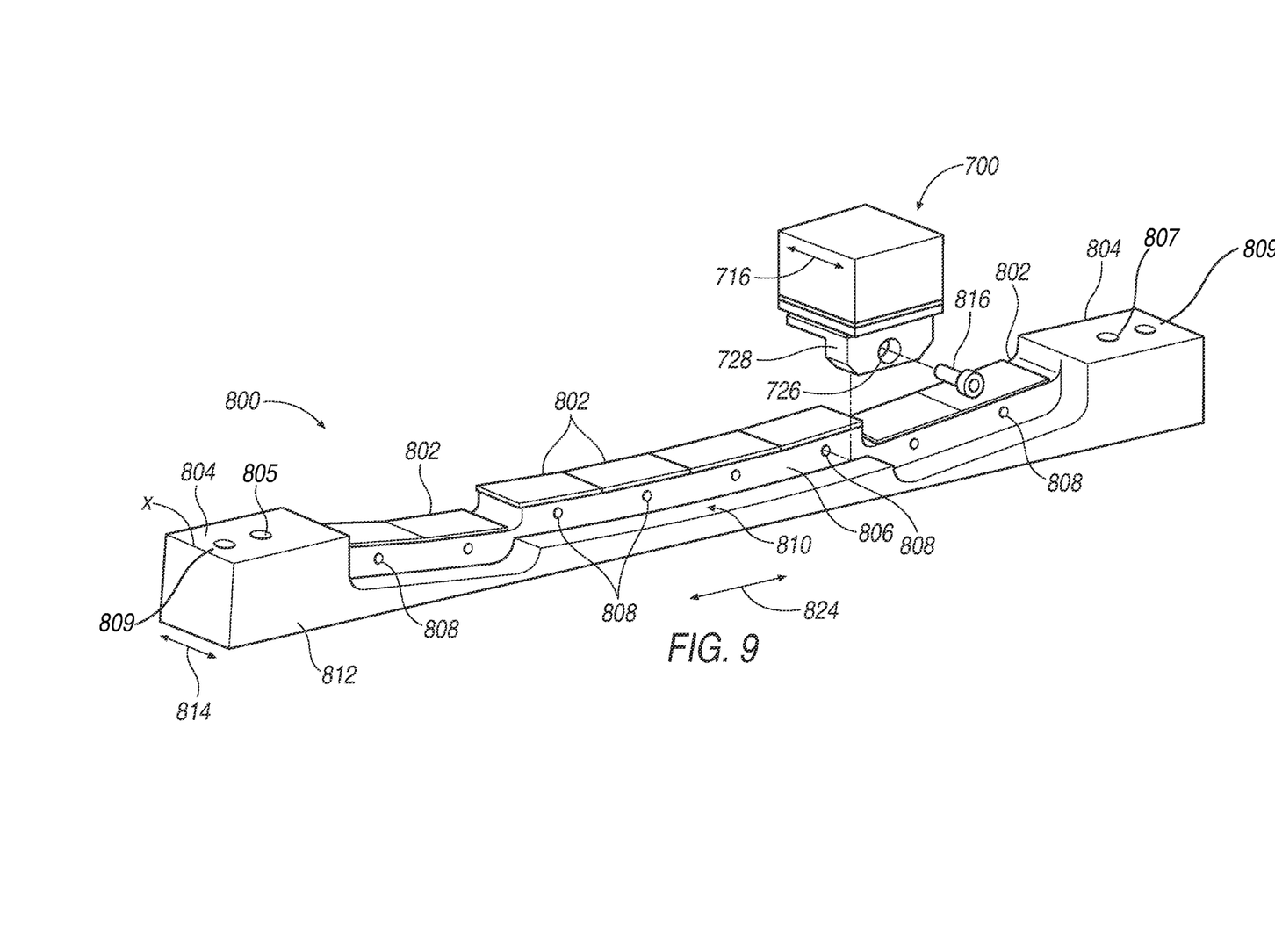
FIG. 9 illustrates a sub-assembly having a module being positioned illustrated thereon.

Referring to FIG. 9, sub-assembly 700 is shown proximate to a support structure 800 according to the disclosure. Support structure 800 includes detector sub-assembly mount or Y-axis mount surfaces 802, on which sub-assemblies 700 are positioned. Y-axis mount surfaces 802 are obliquely positioned such that, when sub-assemblies 700 are positioned thereon, the detectors are positioned in an arc where the focal spot is the center of a corresponding circle. That is, sub-assemblies 700, otherwise referred to as modules 400, are thereby positioned such that plates 444 in anti-scatter grid 442 are slightly non-parallel to one another so that each may be directed and approximately aimed toward focal spot 142 of CT system 100 and such that, when CT detector 130 is positioned in CT system 100, the length of plates 444 extend 446 approximately toward focal spot 142 of CT system 100.

Figure 11:
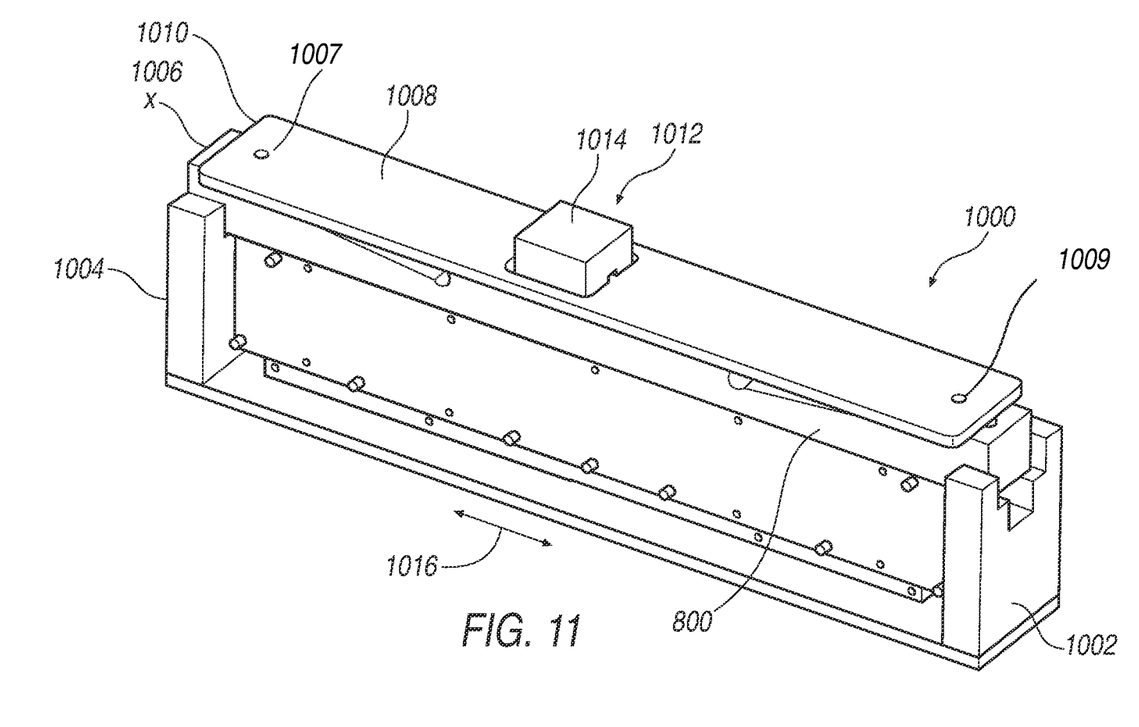
FIG. 11 illustrates a Z-alignment fixture for positioning a center module.

Support structure 800 includes Y-axis mount surfaces 804 and an X-axis mount surface 806. Y-axis surfaces 804 include apertures 805, 807 that correspond with dowl pins 1007, 1009 that are shown in FIG. 11. Apertures 805, 807 in one example are both circular in nature, and in another example one of apertures 805, 807 is an elongated hole or slot, such as an ellipse, having its elongation along a Z-direction 824. Dowl pins 1007, 1009 extend to the underside of a Z-alignment plate 1008 as shown therein, and as will be discussed. Apertures 809 outboard of apertures 805/807 are, in one example, threaded and for mounting to the assembly.

Apertures 808 pass through X-axis mount surface 806 and into support structure 800 and are, in the illustrated example, threaded holes. A cutaway or cavity 810 extends inwardly from an outer X surface 812, having a depth (in x-direction 814) sufficient such that a lower shoulder 728 of sub-assembly 700, extending downward from and orthogonal to Y-axis planar surface 722 (FIGS. 7 and 8), is positioned inboard of outer X surface 812. Mount block 702 thereby forms generally an "L" shape between an upper planar element 730 having top planar surface 720, and lower shoulder 728 orthogonal thereto.

According to the disclosure, aperture 726 of mount block 702 is positioned in lower shoulder 728 such that aperture 726 is aligned, in each mini-module 400, with aperture 808 when Y-axis planar surface 722 is positioned against Y-axis mount surfaces 802 of support structure 800. As illustrated, support structure 800 includes several (8 in the illustrated example) Y-axis mount surfaces 802, and apertures 808 corresponding therewith. In such fashion, eight (in the illustrated example) modules 400 thereby correspond with the eight Y-axis mount surfaces 802 such that apertures 726 in each mini-module 400 align with a respective aperture 808 in support structure 800.

Figure 10:
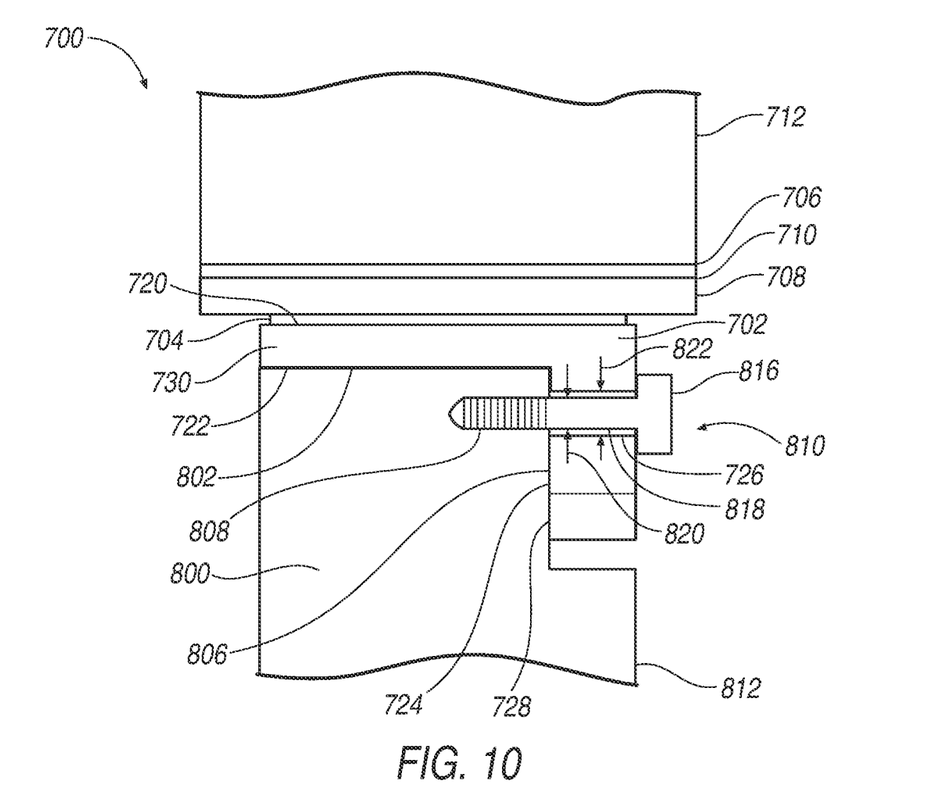
FIG. 10 illustrates a cross-section of a module showing play in a mounting screw.

Mini-modules 400 are aligned with respect to each other according to the disclosure, and mini-modules 400 are attached to structure via mounting screws 816. Referring to FIG. 10, a cross-section of mini-module 400/700 positioned on support structure 800 is shown. As seen therein, module 700 includes mount block 702 having flex circuit 704 (again, not including some portions of flex circuit 704 as shown in FIG. 4, for illustration purposes), and substrate 708 thereon. Module 700 also includes scintillating array 706, substrate 708, and photodiode 710 positioned therebetween (photodiode is very thin and illustrated as a line).

Upper planar element 730 of mount block 702 is positioned on support structure 800 having two surfaces in contact therewith. That is, Y-axis planar surface 722 is positioned against Y-axis mount surface 802 and X-axis planar surface 724, orthogonal to Y-axis planar surface 722, is positioned against X-axis mount surface 806. The side view of FIG. 10 corresponds with the perspective view of FIG. 9, and the mount block is positioned on the mount surface of the support structure so that the holes or apertures align. Mounting screw 816 is used to hold the mount block to the support structure, and as disclosed herein may be aligned with respect to one another prior to tightening mounting screw 816.

Referring to FIG. 10, mounting screw 816 includes a shoulder or otherwise non-threaded surface 818 having an outer diameter 820. Aperture 726 in lower shoulder 728 includes a diameter 822 that, according to the disclosure, is larger than outer diameter 820. In such fashion, when surfaces 722 and 802 are in contact with one another, and surfaces 724 and 806 are in contact with another, module 804 may be aligned with respect to support structure 800 and along Z-direction 824 as shown in FIG. 9. (Z-direction 824 corresponds with Z-direction 420 in FIG. 4 as well as in triad 138 in FIG. 1. Thus, as will be further discussed, when the surfaces are in contact with one another, and mounting screw 816 is inserted and partially screwed into aperture 808 (but not yet tightened) then mini-module 400 may have "play" that can be employed to position mini-module 400 in its position before mounting screw is tightened.

According to the disclosure, mounting screw 816 includes an outer diameter 818 that is smaller than inner diameter 822 of aperture 726 and passes through aperture 726 and into aperture 808 when Y-axis planar surface 722 is on Y-axis mount surface 802. According to the disclosure, in one example mounting screw 816 is a screw. In one example aperture 726 is circular, but it is contemplated that aperture 726 may take on a different shape such as an oblong or elliptical cross section, to allow movement of the module in the Z direction, as an example, while limiting motion in the Y-direction.

According to the disclosure, a first module may be positioned on the support structure using an external fixture as an example. Referring to FIG. 11, an alignment fixture 1000 includes support legs 1002, 1004. Support legs 1002, 1004 allow positioning of support structure 800 positioned therein. As discussed above and with respect to FIG. 9, support structure 800 includes Y-axis mount surfaces 804 and an X-axis mount surface 806. Y-axis surfaces 804 include apertures 805, 807 that correspond with dowl pins 1007, 1009. Apertures 805, 807 in one example are both circular in nature, and in another example one of apertures 805, 807 is an elongated hole or slot, such as an ellipse, having its elongation along a Z-direction 824 (or correspondingly Z-axis 1016 in FIG. 11). Dowl pins 1007, 1009 extend to the underside of a Z-alignment plate 1008 as shown therein, and engage with apertures 805, 807. Because one of apertures 805/807 is a hole, and the other a slot, the hole (such as aperture 805) provides a reference in Z for alignment of a center module 1014.

In another example for positioning along Z-axis 1016, an end surface 1006 is part of support structure 800 (not shown in support structure 800 in FIG. 9, but may be placed at position "X" as shown in FIG. 9 and in FIG. 11). A Z-alignment plate 1008 is positioned having a first end 1010 positioned against end surface 1006. Z-alignment plate 1008 includes a positioning aperture 1012 that is positioned with respect to first end 1010 such that a module, such as a center module 1014, may be positioned in its desired location along a Z-axis 1016. As described, module 1014, corresponding with the previous discussion with respect to mini-module 400, includes apertures that allow for a slight amount of "play" so that the module can be positioned using Z-alignment plate 1008 and prior to tightening down center module 1014. Thus, according to the disclosure, alignment fixture 1000 positions the support structure, and then Z-alignment plate is positioned as appropriately and aperture 1012 is used to place center module 1014. Once positioned, then mounting screw 816, as described above, is tightened to place the center module in its desired location. As further described, both X and Y positions of center module 1014 are established by virtue of the X and Y orientation surfaces being in contact with one another. For illustration purposes, as with FIG. 9, flex circuit 408 and other of its portions are not shown but it is understood that flex circuit extends beneath support structure 800 and is flexibly bent away from alignment fixture 1000 during assembly.

Thus, according to the disclosure, center module 1014 is properly positioned in 3-space and against a reference surface of the support structure (i.e., end surface 1006 for Z placement), and in both X and Y based off of the surfaces in contact between the module and the support structure. Once center module 1014 is positioned and held fast or tight via mounting screw 816, then Z-alignment plate 1008 may be removed, leaving the module in its desired position in 3-space.

Figure 12:
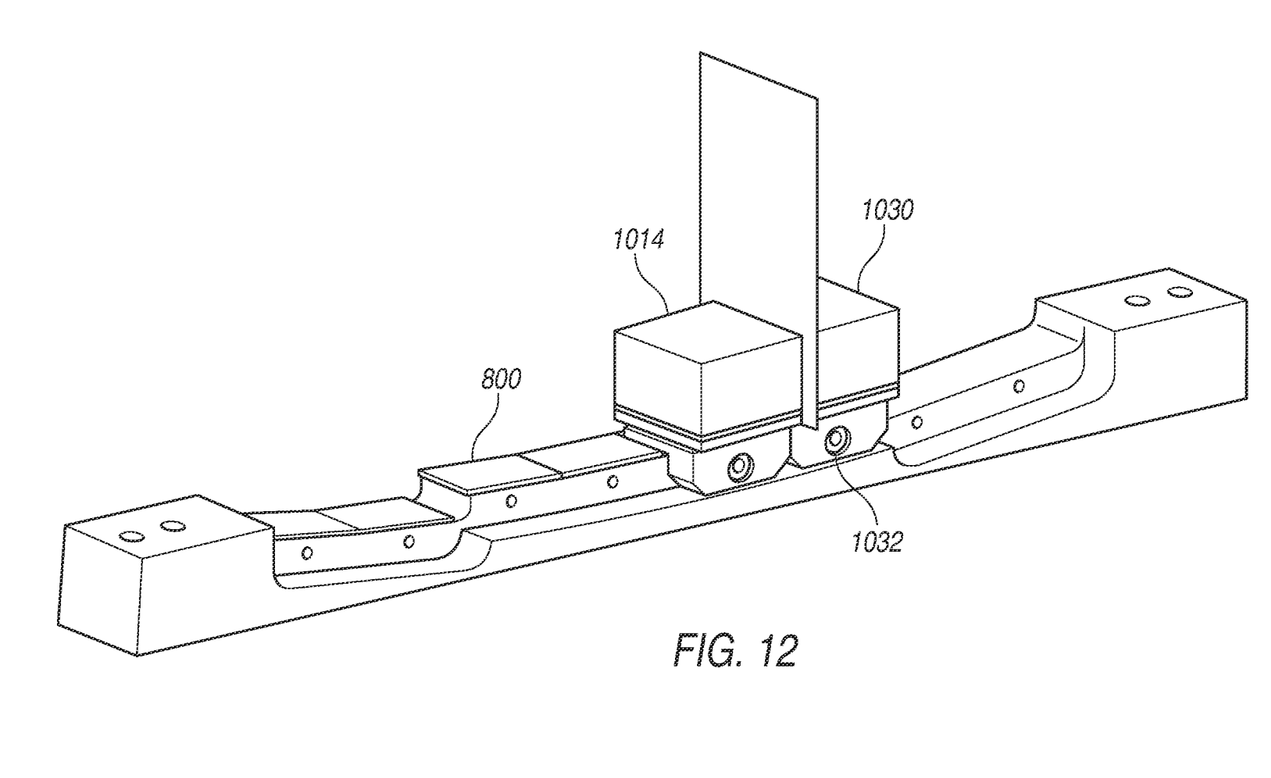
FIG. 12 illustrates a shim for positioning a module with respect to the center module.
Figure 13:
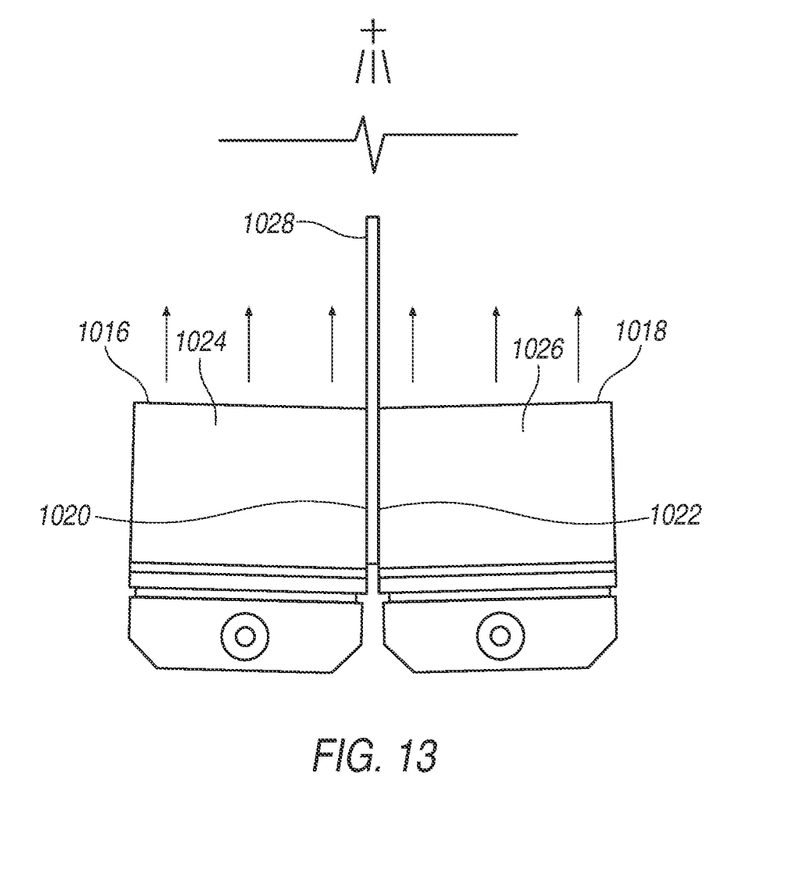
FIG. 13 shows an end view of two modules with a shim used between them to place in a proper Z position with respect to each other.

Referring to FIGS. 12 and 13, subsequent mini-modules 400 are positioned in their proper 3-space position, with respect to the support structure, relative to center module 1014. First referring to FIG. 13, because of a slight angle between two neighboring modules, 1016 and 1018, and because of focused aspects of side walls 1020, 1022 of respective scintillators 1024, 1026, a shim 1028 may be used to position one mini-module with respect to the other, as according to the disclosure side walls 1020, 1022 of their respective ASGs are parallel with one another because of the angle of the walls of the anti-scatter grid, as well as the angle of the mount surfaces on which the modules are placed. Thus, referring to FIG. 12, center mini-module 1014, having been positioned in its desired 3-space position (Z position via the fixture, and X and Y position via the contact of surfaces), then a second mini-module 1030 is then positioned with a set spacing, along the Z axis, by using shim 1028. Shim 1028 establishes a set or desired Z-spacing between center mini-module 1014 and mini-module 1030, and the "play" of the mounting screw 1032 used to hold module 1030 to support structure 800 may be employed prior to tightening mounting screw 1032. That is, as described with respect to FIG. 10, the "play" in each mini-module, established via diametric differences between diameter 820 and 822 is used to enable the preferred placement of the module prior to tightening the module against the support structure.

It is contemplated that, of course, a shim may be used to either side of center mini-module 1014, and in subsequent line with mini-module 1030, so that all mini-modules are placed in their desired 3-space location according to the disclosure.

According to the disclosure, a detector sub-assembly for a CT system includes a detector module that includes a mount block having a top planar surface, a Y-axis planar surface that is parallel with the top planar surface, an X-axis planar surface that is orthogonal to the first Y-axis planar surface, and an aperture passing through the X-axis planar surface. The module includes a substrate having a pixelated photodiode positioned thereon, and a two-dimensional anti-scatter grid (ASG) positioned on the pixelated photodiode. The detector sub-assembly includes a support structure including a Y-axis mount surface and an X-axis mount surface, and a second aperture passing through the X-axis mount surface, a mounting screw having an outer diameter that is smaller than an inner diameter of the aperture and passing through the aperture and into the second aperture when the Y-axis planar surface is on the Y-axis mount surface.

According to the disclosure, a method of assembling a detector assembly for a CT system thereby includes providing a support structure that includes a first Y-axis mount surface and a second Y-axis mount surface, positioning a first detector module on the first Y-axis mount surface, the first detector module including a first mount block having a first top planar surface, a first Y-axis planar surface that is parallel with the first top planar surface, a first X-axis planar surface that is orthogonal to the first Y-axis planar surface, and a first aperture passing through the first X-axis planar surface, a first substrate having a first pixelated photodiode positioned thereon, and a first two-dimensional anti-scatter grid (ASG) positioned on the first pixelated photodiode. The method further includes attaching the first detector module to the first Y-axis mount surface of the support structure by passing a first mounting screw through the first aperture and into a second aperture that is in the support structure, the first mounting screw having an outer diameter that is smaller than an inner diameter of the first aperture.

Also according to the disclosure, a CT system includes a rotatable gantry having an opening for receiving an object to be scanned, an x-ray tube having a focal spot from which x-rays emit, and a detector sub-assembly. The detector sub-assembly includes a first detector module that includes a first mount block having a first top planar surface, a first Y-axis planar surface that is parallel with the first top planar surface, a first X-axis planar surface that is orthogonal to the first Y-axis planar surface, and a first aperture passing through the first X-axis planar surface, a first substrate having a first pixelated photodiode positioned thereon, and a first two-dimensional anti-scatter grid (ASG) positioned on the first pixelated photodiode. A support structure includes a first Y-axis mount surface and a first X-axis mount surface, and a second aperture passing through the first X-axis mount surface, and a first mounting screw having an outer diameter that is smaller than an inner diameter of the of the first aperture and passing through the first aperture and into the second aperture when the first Y-axis planar surface is on the first Y-axis mount surface.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A detector sub-assembly for a CT system, comprising:
   a first detector module that includes:
      a first mount block having a first top planar surface, a first Y-axis planar surface that is parallel with the first top planar surface, a first X-axis planar surface that is orthogonal to the first Y-axis planar surface, and a first aperture passing through the first X-axis planar surface;
      a first substrate having a first pixelated photodiode positioned thereon; and
      a first two-dimensional anti-scatter grid (ASG) positioned on the first pixelated photodiode;
   a support structure including a first Y-axis mount surface and a first X-axis mount surface, and a second aperture passing through the first X-axis mount surface; and
   a first mounting screw having an outer diameter that is smaller than an inner diameter of the first aperture and passing through the first aperture and into the second aperture when the first Y-axis planar surface is on the first Y-axis mount surface.

2. The detector sub-assembly of claim 1, wherein the first mounting screw is a shoulder screw.

3. The detector sub-assembly of claim 1, wherein the first aperture is circular.

4. The detector sub-assembly of claim 1, further comprising a second detector module that includes:
   a second mount block having a second top planar surface, a second Y-axis planar surface that is parallel with the second top planar surface, a second X-axis planar surface that is orthogonal to the second Y-axis planar surface, and a third aperture passing through the second X-axis planar surface;
   a second substrate having a second pixelated photodiode positioned thereon; and
   a second two-dimensional ASG positioned on the second pixelated photodiode;
   the support structure including a second Y-axis mount surface and a second X-axis mount surface, and a fourth aperture passing through the second X-axis mount surface;
   a second mounting screw having an outer diameter that is smaller than an inner diameter of the of the third aperture and passing through the third aperture and into the fourth aperture when the second Y-axis planar surface is on the second Y-axis mount surface.

5. The detector sub-assembly of claim 4, wherein the first Y-axis mount surface and the second Y-axis mount surface are at an oblique angle with respect to each other.

6. The detector sub-assembly of claim 5, wherein the first ASG includes a first outer wall and the second ASG includes a second outer wall, the first outer wall and the second outer wall parallel with one another.

7. The detector sub-assembly of claim 4, wherein the second mounting screw is a shoulder screw, and wherein the third aperture is circular.

8. A method of assembling a detector assembly for a CT system, the method comprising:
   providing a support structure that includes a first Y-axis mount surface and a second Y-axis mount surface;
   positioning a first detector module on the first Y-axis mount surface, the first detector module including:
      a first mount block having a first top planar surface, a first Y-axis planar surface that is parallel with the first top planar surface, a first X-axis planar surface that is orthogonal to the first Y-axis planar surface, and a first aperture passing through the first X-axis planar surface;
      a first substrate having a first pixelated photodiode positioned thereon; and
      a first two-dimensional anti-scatter grid (ASG) positioned on the first pixelated photodiode;
   attaching the first detector module to the first Y-axis mount surface of the support structure by passing a first mounting screw through the first aperture and into a second aperture that is in the support structure, the first mounting screw having an outer diameter that is smaller than an inner diameter of the first aperture.

9. The method of claim 8, wherein providing the first mounting screw comprises providing a first shoulder screw.

10. The method of claim 8, wherein the first aperture is circular.

11. The method of claim 8, further comprising:
    positioning a second detector module on the second Y-axis mount surface, the second detector module including:
       a second mount block having a second top planar surface, a second Y-axis planar surface that is parallel with the second top planar surface, a second X-axis planar surface that is orthogonal to the second Y-axis planar surface, and a third aperture passing through the second X-axis planar surface;

a second substrate having a second pixelated photodiode positioned thereon; and
a second two-dimensional ASG positioned on the second pixelated photodiode;
the support structure including a second X-axis mount surface, and a fourth aperture passing through the second X-axis mount surface;
attaching the second detector module to the support structure by passing a second mounting screw through the third aperture and into the fourth aperture that is in the support structure, the second mounting screw having an outer diameter that is smaller than an inner diameter of the third aperture.

12. The method of claim 11, wherein positioning the first detector module and second detector module comprises positioning such that the first Y-axis mount surface and the second Y-axis mount surface are at an oblique angle with respect to each other.

13. The method of claim 12, wherein the first ASG includes a first outer wall and the second ASG includes a second outer wall, the first outer wall and the second outer wall parallel with one another when the first Y-axis planar surface is on the first Y-axis mount surface, and when the second Y-axis planar surface is on the second Y-axis mount surface;
further comprising positioning a shim between the first outer wall and the second outer wall, to position the second detector module with respect to the first detector module prior to attaching the second detector module to the support structure.

14. The method of claim 13, wherein the second mounting screw is a shoulder screw, and wherein the third aperture is circular.

15. A CT system comprising:
a rotatable gantry having an opening for receiving an object to be scanned;
an x-ray tube having a focal spot from which x-rays emit; and
a detector sub-assembly comprising:
a first detector module that includes:
a first mount block having a first top planar surface, a first Y-axis planar surface that is parallel with the first top planar surface, a first X-axis planar surface that is orthogonal to the first Y-axis planar surface, and a first aperture passing through the first X-axis planar surface;
a first substrate having a first pixelated photodiode positioned thereon; and
a first two-dimensional anti-scatter grid (ASG) positioned on the first pixelated photodiode;
a support structure including a first Y-axis mount surface and a first X-axis mount surface, and a second aperture passing through the first X-axis mount surface;
a first mounting screw having an outer diameter that is smaller than an inner diameter of the first aperture and passing through the first aperture and into the second aperture when the first Y-axis planar surface is on the first Y-axis mount surface.

16. The CT system of claim 15, wherein the first mounting screw is a shoulder screw.

17. The CT system of claim 15, wherein the first aperture is circular.

18. The CT system of claim 1, the detector sub-assembly further comprising a second detector module that includes:
a second mount block having a second top planar surface, a second Y-axis planar surface that is parallel with the second top planar surface, a second X-axis planar surface that is orthogonal to the second Y-axis planar surface, and a third aperture passing through the second X-axis planar surface;
a second substrate having a second pixelated photodiode positioned thereon; and
a second two-dimensional ASG positioned on the second pixelated photodiode;
the support structure including a second Y-axis mount surface and a second X-axis mount surface, and a fourth aperture passing through the second X-axis mount surface;
a second mounting screw having an outer diameter that is smaller than an inner diameter of the of the third aperture and passing through the third aperture and into the fourth aperture when the second Y-axis planar surface is on the second Y-axis mount surface.

19. The CT system of claim 18, wherein the first Y-axis mount surface and the second Y-axis mount surface are at an oblique angle with respect to each other, wherein the first ASG includes a first outer wall and the second ASG includes a second outer wall, the first outer wall and the second outer wall parallel with one another.

20. The CT system of claim 19, wherein the second mounting screw is a shoulder screw, and wherein the third aperture is circular.

* * * * *